US00PP12680P2

(12) United States Plant Patent
Verweij

(10) Patent No.: US PP12,680 P2
(45) Date of Patent: Jun. 4, 2002

(54) HIBISCUS PLANT NAMED 'MARINA'

(75) Inventor: Rien Verweij, Boskoop (NL)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 09/566,451

(22) Filed: May 8, 2000

(51) Int. Cl.[7] ..... A01H 5/00

(52) U.S. Cl. ..... Plt./257

(58) Field of Search ..... Plt./257

*Primary Examiner*—Bruce R. Campell
*Assistant Examiner*—Wendy C Baker
(74) *Attorney, Agent, or Firm*—C. A. Whealy

(57) ABSTRACT

A distinct cultivar of Hibiscus plant named 'Marina', characterized by its upright plant habit; very freely branching; dense and bushy growth habit; freely flowering habit; and attractive and numerous violet blue-colored flowers.

1 Drawing Sheet

BACKGROUND OF THE INVENTION

The present Invention relates to a new and distinct cultivar of Hisbiscus plant, botanically known as *Hibiscus syriacus*, and hereinafter referred to by the cultivar name Marina.

The New Hibiscus is a product of a breeding program conducted by the Inventor in Boskoop, The Netherlands. The objective of the breeding program was to create new Hibiscus cultivars with good vigor and violet blue-colored flowers.

The new Hibiscus originated from open-pollinations of various unidentified seedling selections *Hibiscus syriacus* cultivar Oiseau Bleu, not patented, in 1995. The new Hibiscus was discovered and selected by the Inventor in 1996 as a single flowering plant within the progeny from these crosses in a controlled environment in Boskoop, The Netherlands. The new Hibiscus was selected on the basis of its vigor and desirable violet blue flower color.

Asexual reproduction of the new cultivar by cuttings taken at Boskoop, The Netherlands, has shown that the unique features of this new Hibiscus are stable and reproduced true to type in successive generations.

SUMMARY OF THE INVENTION

Plants of the cultivar Marina have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Marina'. These characteristics in combination distinguish 'Marina' as a new and distinct cultivar:

1. Upright plant habit.

2. When pinched, very freely branching; dense and bushy growth habit.

3. Freely flowering.

4. Attractive and numerous violet blue-colored flowers.

Compared to the unidentified selections of the *Hibiscus syriacus* cultivar 'Oiseau Bleu', plants of the new Hibiscus are faster-growing, have longer lateral branches, are more freely branching, and are therefore more densely foliated and are much more freely flowering.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ from the color values cited in the detailed botanical description which more accurately describe the actual colors of the new Hibiscus. The photograph comprises a close-up view of a typical flower of 'Marina'.

DETAILED BOTANICAL DESCRIPTION

In the following description, color references are made to The Royal Horticultural Society Colour Chart except where general terms of ordinary dictionary significance are used. Plants were grown in Grand Haven, Mich. under field conditions which closely approximate commercial production conditions. Plants used for the description were about four years old.

Botanical classification: *Hibiscus syriacus* cultivar Marina.

Parentage: Open-pollination of various unidentified seedling selections of *Hibiscus syriacus* cultivar Oiseau Bleu, not patented.

Propagation:

*Type cutting*.—By softwood or hardwood cuttings.

*Time to initiate roots*.—Summer: About 21 days at 32° C. Winter: About 28 days at 20° C.

*Time to produce a rooted cutting or liner*.—Summer: About 56 days at 32° C. Winter: About 70 days at 20° C.

*Root description* . —Thick and fleshy.

Plant description:

*Crop time*.—From cuttings, about one growing season is required to produce a flowering finished plant in a one-gallon container.

*Form*.—Mostly upright; inverted triangle; dense and bushy perennial.

*Usage*.—Appropriate for one to three-gallon containers.

*Plant height, soil level to top of plant plane*.—About 2.7 m.

*Plant width*.—About 1.75 m.

*Vigor*.—Moderately rapid growth rate.

*Branching habit*.—When pinched, very freely branching with about 29 lateral branches per plant.

*Lateral branches*.—Length: About 75 cm. Diameter: About 6.5 mm. Internode length: About 4.5 cm. Texture: Smooth. Color: 177 A.

*Foliage description*.—Leaves simple, generally symmetrical and long persisting. Tolerant to stresses. Quantity per lateral branch: Typically about 50. Length: About 7.5 cm. Width: About 4.75 cm. Shape: Rhomboid to ovate, three-lobed. Apex: Acute. Base: Broadly cuneate to rounded. Margin: Crenate; undulate. Texture: Glabrous; thick. Color: Young foliage, upper surface: 146A. Young foliage, lower surface: 146B. Mature foliage, upper surface: 146A; venation, 146B. Mature foliage, lower surface: 146B; venation, 146C. Petiole: Length: About 1.65 cm. Diameter: About 2 mm. Color: 146B.

Flower description:

*Flower type and habit*.—Single rounded flowers arising from leaf axils. Freely flowering. Flowers last about one day on the plant. Not persistent. Not fragrant.

*Natural flowering season*.—Continuously flowering from mid-summer through fall.

*Quantity of flowers*.—About 33 per lateral branch, about 957 per plant during the growing season.

*Flower diameter*.—About 10.5 cm.

*Flower depth* (*height*).—About 2.5 cm.

*Flower buds* (*just showing color*).—Length: About 4.5 cm. Diameter: About 2.25 cm. Shape: Elliptical. Rate of opening: About one day.

*Petals*.—Arrangement/appearance: Single whorl of five petals. Length: About 5.75 cm. Width: About 5 cm. Shape: Obovate. Apex: Rounded to obtuse. Margin: Entire; undulate. Surface: Veins slightly raised. Texture: Smooth. Color: Upper surface, when opening: 98C; base and veins, 61A. Lower surface, when opening: 98C. Upper surface, opened flower: 98C; base and veins, 61A; becoming darker, 89B, with subsequent development. Lower surface, opened flower: 98C.

*Calyx*.—Shape: Star; sepals, five. Length: About 2 cm. Diameter: About 1.5 cm. Sepal shape: Narrowly deltoid; apex, acute; margin, entire. Texture: Smooth; thick. Color: Upper surface: 145A. Lower surface: 144A.

*Peduncle*.—Strength: Moderately strong. Angle: About 25° to the stem. Length: About 1.5 cm. Color: 138A.

*Reproductive organs*.—Stamens: Anther length: About 1 mm. Anther color: 11B. Pollen amount: Moderate. Pollen color: 11B. Pistils: Pistil quantity per flower: One. Pistil length: About 3 cm. Stigma shape: Five-parted; rounded. Stigma color: White, close to 155D. Style length: About 3 cm. Style color: White, close to 155D. Ovary color: 193B.

*Seed*.—Length: About 5 mm. Diameter: About 4 mm. Color: 198B.

Disease resistance: Under commercial productions, plants of the new Hibiscus have not been noted to be resistant to pathogens common to Hibiscus.

Insect resistance: Under commercial production conditions, plants of the new Hibiscus have been noted to be resistant to slugs.

It is claimed:

1. A new and distinct cultivar of Hibiscus plant named 'Marina', as illustrated and described.

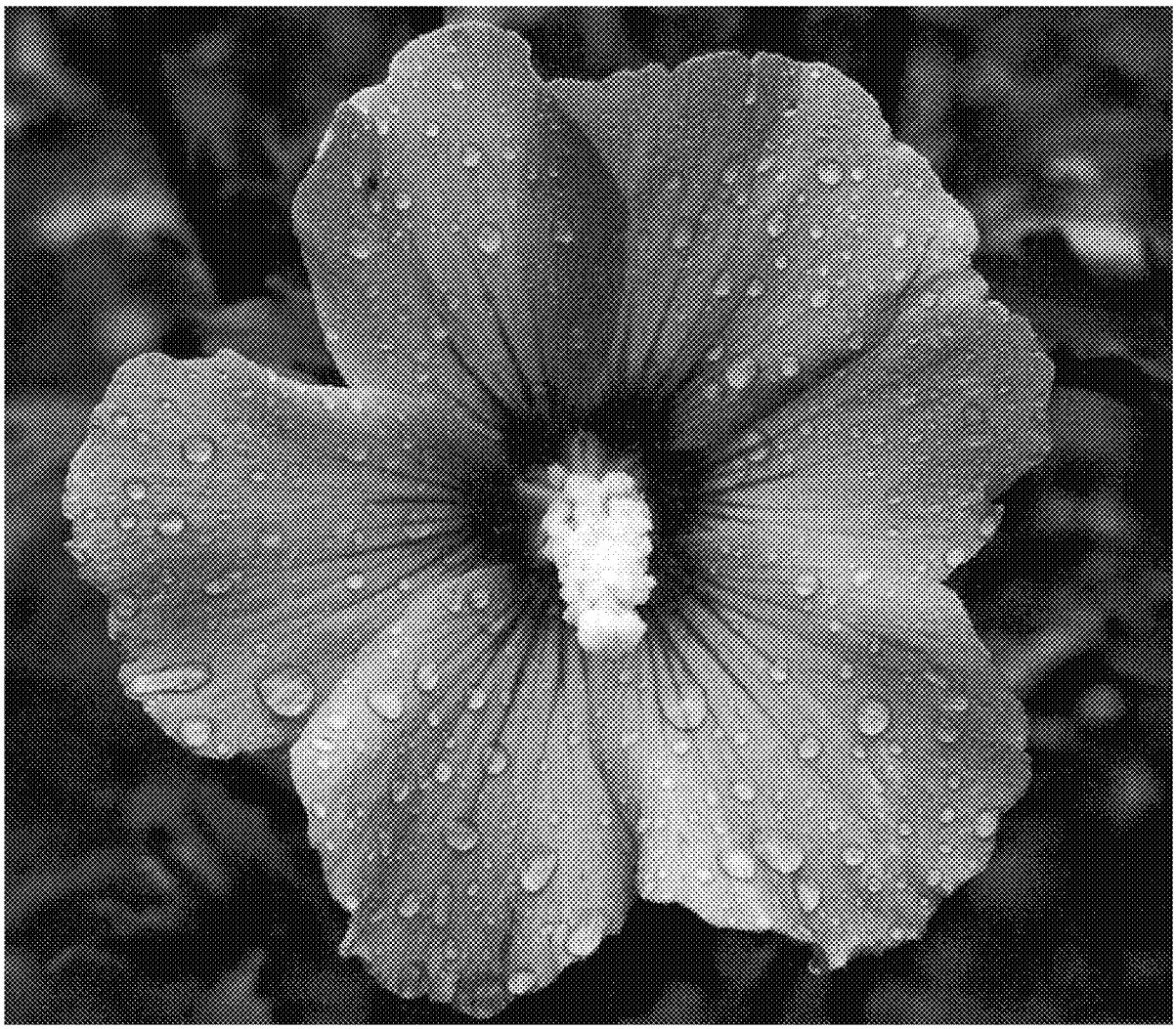

* * * * *